(12) United States Patent
Walton (10) Patent No.: US 7,160,536 B2
(45) Date of Patent: Jan. 9, 2007

(54) RADIOLABELLED METAL TRANSPORT PROTEINS AS IMAGING AGENTS (75) Inventor: Paul Walton, York (GB)

(73) Assignee: Vistatec York Limited, York (GB)

(*) Notice: Subject to any disclaimer, the term of this patent is extended or adjusted under 35 U.S.C. 154(b) by 170 days.

(21) Appl. No.: 10/344,079

(22) PCT Filed: Aug. 7, 2001

(86) PCT No.: PCT/GB01/03531

§ 371 (c)(1),
(2), (4) Date: Jul. 24, 2003

(87) PCT Pub. No.: WO02/11772

PCT Pub. Date: Feb. 14, 2002

(65) Prior Publication Data

US 2004/0013675 A1 Jan. 22, 2004

(30) Foreign Application Priority Data

Aug. 8, 2000 (GB) ................................. 0019412.6

(51) Int. Cl.
*A61K 51/00* (2006.01)
*A61M 36/14* (2006.01)
(52) U.S. Cl. .................... 424/1.69; 424/1.11; 424/1.65

(58) Field of Classification Search ............... 424/1.11, 424/1.65, 1.69; 206/569, 570, 223; 534/10, 534/14
See application file for complete search history.

(56) References Cited

U.S. PATENT DOCUMENTS 4,057,617 A 11/1977 Abramovici et al.

FOREIGN PATENT DOCUMENTS

WO WO 94/01773 AI 1/1994

OTHER PUBLICATIONS

Welling et al (European Journal of Nuclear Medicine, Mar. 2000, vol. 27, No. 3, pp. 292-301).*
Vanlić-Razumenić et al., Interaction of $^{99m}$Tc-radiopharmaceuticals with Transport Proteins in Human Blood, Nucl. Med. Biol., vol. 20, No. 3, pp. 363-365, 1993.

* cited by examiner

*Primary Examiner*—Dameron L. Jones
(74) *Attorney, Agent, or Firm*—Myers Bigel Sibley & Sajovec, PA (57) ABSTRACT A $^{99mc}$Tc labeled metal transport protein, products and uses thereof in imaging and especially detecting the presence of high energy/iron uptake tissues such as a tumour within a mammalian body are provided.

19 Claims, 8 Drawing Sheets

RADIOLABELLED METAL TRANSPORT PROTEINS AS IMAGING AGENTS

CROSS-REFERENCE TO RELATED APPLICATIONS

The present application is a 35 U.S.C. §371 national phase application of PCT International Application No. PCT/GB01/03531, having an international filing date of Aug. 7, 2001, and claiming priority to Great Britain Patent Application No. 0019412.6, filed Aug. 8, 2000, the disclosures of which are incorporated herein by reference in their entireties. The above PCT International Application was published in the English language and has International Publication No. WO 02/11772 A2.

The present invention relates to a radiolabeled metal transport protein and use thereof, the radiolabeled metal transport protein being for use particularly, but not exclusively, in imaging tumour sites within a mammalian body.

BACKGROUND TO THE INVENTION

In nuclear medicine, various techniques have been used to visualise the presence of a tumour within a body. In quantitative terms, technetium (Tc) compounds are by far the most important radiopharmaceuticals used today with an estimated market share of more than 80%.

For radiomedical purposes, the isotope $^{99}$Tc is important not in its slowly β-decaying ground state but in a metastable, nuclear excited state, i.e. as exclusively γ-emitting $^{99m}$Tc with a diagnostically useful half-life of six hours. One of the major reasons for the popularity of this radioisotope in radiodiagnostics is the availability of an easily operable technetium 'reactor' or 'generator', which allows the convenient preparation of applicable solutions in a normal clinical environment.

It is known from the prior art to use the pertechnetate anion $[^{99m}TcO_4]^-$ for medical imaging of thyroid disease, based on the principle that the pertechnetate anion would behave similarly to iodine and be taken up by the thyroid. The pertechnetate anion has also been used to image heart, brain, kidney and liver. However, a growing demand for more specific imaging agents has led to the development of covalently linking an appropriate technetium complex to a small peptide or biologically active molecule (BAM). Examples known from the prior art include: $Tc^V$ complexes linked to bisamidedithiol proligands such as ethylenecysteine diester for use in imaging cerebral blood flow in the brain; $^{99m}$Tc-teboroxime and $^{99m}$TcN-NOET for imaging the heart disease; $^{99m}$Tc-HIDA, $^{99m}$Tc-Lidofenein, $^{99m}$Tc-Mebrofenin for imaging the hepatobilary system; $^{99m}$Tc-diethylenetriaminepentaacetic acid for imaging kidney disease; and $^{99m}$Tc-complexes of phosphonate ligands for imaging bone disease. However whilst these compounds are tissue specific none of them is specific for tumour detection.

Further developments in the use of $^{99m}$Tc in medical imaging are based on adapting the outer surface of a technetium complex so as to contain groups necessary for receptor binding. For example, such developments include labelling progesterone receptors with $^{99m}$Tc to identify breast tumours, labelling central nervous system receptors with $^{99m}$Tc to identify psychiatric conditions, epilepsy and Alzheimer's disease and labelling a variety of antibodies with $^{99m}$Tc.

The problem associated with this group of prior art compounds is that, whilst they may be tissue specific, only $^{99m}$Tc labelled progesterone receptors and $^{99m}$Tc labelled tumour antibodies can be considered as tumour specific imaging agents. Moreover, these compounds are expensive, laborious and difficult to make and often are quite difficult to handle.

A $^{99m}$Tc labelled imaging agent that is cell selective, inexpensive and simple to make would offer immediate advantage over the prior art.

In the present invention we have exploited the characteristics of cell behaviour and developed a naturally occurring protein which we have labelled with $^{99m}$Tc.

Amongst other characteristics/factors, tumour cells can be distinguished from normal cells by their rapid rate of proliferation. A rapid rate of cellular proliferation creates a high energy requirement in tumour cells for most cellular processes, including a high demand on metal transportation into the cell by metal transport proteins.

One such group of metal transport proteins are transferrins which includes lactoferrin and, being naturally occurring proteins within the body with a transport function, transferrins inherently transport across all membranes, including the blood-brain barrier. The mechanism by which transferrins enter the cells and release iron into the cells is as follows. Circulating transferrin is bound to a specific receptor on the cell surface and is subsequently taken up as a receptor/transferrin complex by endosomes into the cytosol. Once the receptor/transferrin complex is in the cytosol the receptor/transferrin complex releases the $Fe^{3+}$ or "demetallates" and the apotransferrin and receptor are released back out through the cytosol to the cell surface where they may be degraded, or recycled.

We have used the inherent ability of metal transport proteins to target cells combined to develop the imaging agents of the present invention.

Accordingly we believe that the present invention, in one aspect, provides tumour-specific imaging agents which will assist the clinician to make an early clinical diagnosis without the need for invasive exploratory investigation.

SUMMARY OF THE INVENTION

In its broadest aspect the present invention relates to a $^{99m}$Tc labelled metal transport protein and uses thereof in imaging and especially detecting the presence of a tumour within a mammalian body.

According to a first aspect of the invention, there is provided a $^{99m}$Tc labelled metal transport protein complex.

Preferably, the metal transport protein is an iron transport protein and more preferably is a transferrin preferably selected from the group comprising lactoferrin, ovotransferrin and/or serum transferrin. When the metal transport protein is a transferrin it is preferentially taken up by tumour cells because of their high energy demand and rate of proliferation.

Reference herein to transferrin is intended to include lactoferrin, ovotransferrin and/or serum transferrin in their apoprotein or metal-loaded states.

It will be appreciated that the labelled metal transport protein complex of the present invention carries $^{99m}$Tc in the sites normally occupied by the metal ions. In the embodiment where the metal transport protein is a transferrin, the protein carries $^{99m}Tc^{3+}$ in place of $Fe^{3+}$ ions and encapsulates or folds around the two binding sites occupied by $^{99m}Tc^{3+}$ in a similar way as the transferrin glycoprotein would accommodate $Fe^{3+}$ ions in the natural state. Accordingly, the shape/configuration of the Tc-transferrin is not dramatically distorted or substantially altered from that of the naturally occurring Fe-transferrin complex. It is because the $^{99m}$Tc-labelled transferrin complex is similar in structure to endogenous Fe$^{3+}$ carrying transferrins that the $^{99m}$Tc labelled transferrin complex is likely to be recognised by cells and taken up and processed as an endogenous transferrin.

Rapidly dividing cells such as tumour cells have high energy and nutrient requirements and have increased demands on a number of normal cellular metabolic processes/activities. Amongst these increased requirements is a demand for iron. By utilising the iron metal transport proteins as carriers for $^{99m}$Tc, one embodiment of the present invention offers a tumour imaging agent that will naturally be attracted to areas within the body that have high iron demand. Similarly, other metal transport proteins can be used for selectively targeting tissues/sites within the body.

Preferably, the metal transport protein is derived from mammalian tissue or blood and more preferably is a recombinant protein.

Recombinant protein is of particular advantage in that the risk of cross haematological infection from other factors/agents present in whole blood, such as by hepatitis virus or HIV, is obviated. Moreover, there is a current abundance of recombinant lactoferrin that is commercially available so that a further advantage of the invention resides in the reduced cost of the complex compared to other prior art compounds/complexes. The recombinant protein may be modified as compared with the natural protein, provided that it retains functional metal transport and receptor binding properties.

According to another aspect of the invention there is provided use of a $^{99m}$Tc labelled metal transport protein as an imaging agent especially but not exclusively, in detecting the presence of a tumour within a mammalian body.

Preferably, the $^{99m}$Tc labelled metal transport protein further includes any one or more of the preferred features hereinbefore described.

The present invention therefore provides an alternative imaging agent from the prior art.

According to a yet further aspect of the invention there is provided a product or composition comprising a metal transport protein and a reducing agent, the function of the reducing agent being to convert Tc as the pertechnetate (TcO$_4^-$) to Tc$^{3+}$ so that it may bind to the protein. In this respect the reducing agent may comprise any agent that is capable of performing the reduction step.

Preferably, the metal transport protein is as hereinbefore described.

Preferably, the product comprises an amount of metal transport protein in the range of 2–60 mg.

Preferably, the product or composition further includes a $^{99m}$Tc source, more preferably the source is pertechnetate i.e. TcO$_4^-$. The pertechnetate source can be provided with the product or composition in a suitable vial or vessel or it may be provided separately therefrom and added to the metal transport protein and reducing agent shortly before use. Typically, the pertechnetate source is, provided as a solution; typically it is generated at the site where the investigation/treatment is to take place.

Preferably, the amount of $^{99m}$Tc in the product, when labelled with $^{99m}$Tc, is in the range of 6–8 GBq and more preferably is about 7.4 GBq (200 mCi).

Preferably, the reducing agent is selected from the group comprising a tin(II) salt including, for example, chloride, nitrite and/or sulphite. Another prepared reducing agent is ascorbic acid/ascorbate.

Preferably, the product comprises an amount of reducing agent in the range of 0.2–0.3 mg.

Preferably, the product or composition further includes a solubilising agent and/or an isotonic agent.

Reference herein to an isotonic agent is intended to mean any agent which is capable of rendering the composition to an isotonic state in solution with respect to the pH and ionic strength of blood, so that upon introduction of the product or composition into a body the recipient does not enter a state of shock or suffer any adverse effect to the pH and ionic strength of the composition in solution.

Preferably, the solubilising agent is gentisic acid. The purpose of the solubilising agent is to enable solubilisation of the Tc$^{3+}$ so as to facilitate formation of the metal/protein complex, and therefore the example provided merely illustrates one suitable compound and is not intended to limit the scope of the application.

Preferably, the product comprises an amount of solubilising agent in the range of 0.7–0.9 mg.

Preferably, the isotonic agent comprises a salt and more preferably is sodium chloride.

Preferably, the product comprises an amount of the isotonic agent in the range of 20–40 mg.

Preferably the product or composition is lyophilised, that is to say it is freeze dried.

Preferably, the product or composition is pyrogen-free.

Preferably, the product or composition is provided in powder form.

According to a further aspect of the invention there is provided a method of making a $^{99m}$Tc labelled metal transport protein complex comprising mixing a metal transport protein with a $^{99m}$TcO$_4^-$ source in the presence of a reducing agent.

Preferably, the metal transport protein and reducing agent as hereinbefore described are provided in a sealed vial or vessel which optionally further includes any one or more of the additives hereinbefore described.

Prior to administration, a suitable volume of an appropriate aqueous solution is added to a vial containing the metal transport protein and reducing agent. In practice, the vial is subsequently agitated and allowed to stand for a short period, to ensure that the components have dissolved into the aqueous medium.

Preferably, the $^{99m}$TcO$_4^-$ source is introduced into the resultant aqueous medium as an appropriate aliquot. Alternatively, the $^{99m}$Tc source may be provided with the metal transport protein and/or reducing agent and the aqueous medium as well as any necessary additional components which can be added thereto. It will be appreciated that the reducing agent converts the pertechnetate into a form of $^{99m}$Tc that is taken up by the metal transport protein so that the resultant complex is labelled.

According to a further aspect of the invention there is provided use of a metal transport protein for the manufacture of a $^{99m}$Tc labelled imaging agent for imaging and especially for diagnosing the presence of a tumour site within a mammalian body.

According to a further aspect of the invention there is provided use of a metal transport protein and a reducing agent for the manufacture of an imaging agent for imaging and especially for diagnosing the presence of a tumour site within a mammalian body.

According to a further aspect of the invention there is provided use of pertechnetate for the manufacture of a $^{99m}$Tc labelled metal transport protein complex imaging agent for imaging and especially for diagnosing the presence of a tumour site within a mammalian body.

According to a yet further aspect of the invention there is provided a method of detecting the presence of a tumour within a mammalian body comprising the steps of:
(i) mixing a metal transport protein with an effective amount of pertechnetate in the presence of a reducing agent and an aqueous medium so as to produce a $^{99m}$Tc labelled metal transport protein complex,
(ii) introducing the resultant aqueous medium into a recipient under investigation, and
(iii) observing images of $^{99m}$Tc within the recipient's body over a selected period.

Preferably, the mixture contains any one or more of the additives and/or features hereinbefore described.

Preferably, the composition in solution is injected into the recipient's body, more preferably it is injected by the intravenous route. Alternatively the composition can be taken orally.

According to a yet further aspect of the invention there is provided a method for detecting a tumour comprising observing images of $^{99m}$Tc introduced into a patient as a labelled metal transport protein complex.

According to a yet further aspect of the invention there is provided use of the method as hereinbefore described for detecting/diagnosing the presence of a brain tumour.

Reference herein to brain tumour is intended to include any type of tumour or growth which occurs within the blood-brain barrier.

The product or composition and methods of the present invention which use transferrins are particularly well suited to the detection of the presence of a brain tumour in an individual because of the natural uptake and recognition of the transferrin complex and the inherent ability of transferrins to cross the blood-brain barrier. In this respect the present invention provides significant advantages over the prior art by provision of a specific tumour-selective imaging agent that is able to access all areas of brain tissue.

It will be understood from the foregoing statements of invention that $^{99m}$Tc labelled metal transport protein complexes provide a convenient and cost effective means of detecting the presence of tumours within a mammalian body. The present invention in addition provides a method of treating the tumours once they have been located/identified by using the metal transport protein to carry a radionuclide.

According to a yet further aspect of the invention there is provided a method of treating a tumour detected using a method or product of the invention comprising the steps of:
(i) labelling a metal transport protein with a radionuclide,
(ii) producing an aqueous formulation of the radionuclide labelled metal transport protein, and
(iii) introducing the aqueous formulation into a recipient under treatment.

Preferably, the method further includes the step of, prior to step (i), detecting the presence of a tumour with the $^{99m}$Tc labelled metal transport protein complex of the present invention.

Preferably, the radionuclide labelled metal transport protein complex further includes any one or more of the features hereinbefore described.

Preferably, the aqueous formulation of the radionuclide labelled metal transport protein further includes any one or more of the additives hereinbefore described.

The method thus provides a means of firstly locating a tumour and subsequently ensuring that a further dose of a metal transport protein labelled with a radionuclide is directed to the same location. The radionuclide labelled metal transport protein is thus able to attack/target tumour cells specifically. In this way the combined therapy can act as a locator and destroyer treatment for tumour cells. As previously mentioned, this combined therapy is envisaged to be of particular importance in the diagnosis and treatment of brain tumours because transferrins are able to cross the blood-brain barrier.

Preferably the radionuclide is selected from the group comprising $^{57}$Co, $^{67}$Cu, $^{67}$Ga, $^{90}$Y, $^{97}$Ru, $^{169}$Yb, $^{186}$Re, $^{188}$Re, $^{203}$Pb, $^{153}$Sm and/or $^{212}$Bi.

According to a yet further aspect of the invention there is provided a kit comprising the product or composition of the invention in a suitably sealed vial or vessel and, optionally, a set of written instructions.

According to a yet further aspect of the invention there is provided a kit comprising the product or composition of the invention in a suitably sealed vial or vessel and a further product or composition comprising a radionuclide labelled metal transport protein complex in a suitably sealed vial or vessel and optionally, a set of written instructions.

The invention will now be described by way of example only with reference to the following Figures wherein:

BRIEF DESCRIPTION OF THE DRAWINGS

FIG. 6B illustrates the absorption peak at 231 nm.

FIG. 6C illustrates the 500 nm region in more detail, X representing absorption peak at 0 and 15 minutes, Y representing maximum absorption wavelength at the end of the time course.

EXAMPLES

DETAILED DESCRIPTION OF EMBODIMENTS OF THE INVENTION

Iron containing proteins are known to consist of a single polypeptide chain of around 700 amino acid residues. Both lactoferrin-and transferrin consist of two lobes, the N-lobe and the C-lobe which have about 40% internal sequence homology between them and very similar tertiary structure. The folding is identical in the two lobes but the C terminus lobe contains three extra disulfide bridges, giving it extra stability. Each lobe has a cleft in which the iron atom sits, and binding induces a conformational change causing the lobe to close over the metal. Coordination to the metal is by two tyrosine residues, a histidine and an asparagine. There is also synergistic binding of a bidentate carbonate ligand giving an overall six coordinate, distorted octahedral geometry. The presence of the carbonate is necessary for strong metal binding. The ligands are attached to different parts of the protein backbone which allows the lobes to adopt a more open structure in order to release the iron.

Metal binding to transferrin produces new absorption bands in the UV/vis spectra, due to the binding to the two tyrosinate residues. UV/vis spectroscopy therefore provides a method to distinguish between binding at the iron site compared to other sites such as platinum binding. UV/vis spectroscopy has also been used in conjunction with titration experiments to study the kinetics of binding and to obtain binding constants for a variety of metal transferrin complexes. Herein we have used the same method to determine the binding of rhenium and technetium to transferrin and lactoferrin.

Tumour cells are known to uptake transferrin at a higher rate than healthy cells, and so incorporation of Tc into transferrin and lactoferrin advantageously provides a new method for imaging cancers. Our initial experiments with rhenium whose chemistry is similar to technetium have led us to the present invention.

Example 1

Metal/Protein Binding

Experimental Procedure

Bovine apotransferrin was washed three times with 0.1 M KCl using Centricon 30 ultra-filters to remove low molecular mass impurities. It was dissolved in 10 cm$^3$ of 10 mM Hepes buffer (pH 7.4) and stored in a refrigerator. Apolactoferrin was prepared from Fe-lactoferrin using standard procedures. All glassware was acid soaked for several hours before use to remove any traces of heavy metals and ultrapure water was used in all experiments. Due to its hygroscopic nature, $Re_2O_7$ was stored and weighed in a glove box, to ensure accuracy in measurements.

A Perkin-Elmer Lambda 15 spectrophotometer was used for UV/vis experiments, with 10 mM Hepes buffer solution as background correction.

Preparation of $Re(NTA)_n$

NTA refers to nitrilotriacetate, and n is the amount of NTA present in solution relative to rhenium. Re(NTA), where n is equal to 1, was prepared by adding 4.17 cm$^3$ of NTA solution (0.006 M) to 2.30 cm$^3$ of Re atomic absorption standard solution (1010 µg/ml in 1% $HNO_3$). Slow addition of microlitre amounts of 1 M NaOH was carried out to give a pH of between 5 and 6. This solution was then made up to 25 cm$^3$ with 10 mM Hepes buffer (pH 7.4), to give an overall rhenium concentration of 0.5 mM. $Re(NTA)_8$ and $Re(NTA)_{20}$ were made in the same way but using 8.34 cm$^3$ and 20.85 cm$^3$ of NTA (0.024 M) respectively.

Preparation of $Fe(NTA)_2$

A 0.01 M solution of Fe(III) nitrate was prepared and 2.50 cm$^3$ were added to 16.66 cm$^3$ (2 molar equivalents) NTA solution (0.006 M). This was made up in the same way as Re(NTA) to give a 0.5 mM $Fe(NTA)_2$ solution buffered at pH 7.4 with 10 mM Hepes UV Spectroscopy Initially the band at $\epsilon_{280}$93,000 M$^{-1}$ cm$^{-1}$ was used to determine the concentration of washed apotransferrin by UV spectrometry. UV samples were then prepared by diluting transferrin or lactoferrin to approximately 10$^{-5}$ M by making the volume up to 3000 µl with 10 mM Hepes buffer. Immediately before addition of the metal, 60 µl of $NaHCO_3$ (0.25 M) were added to give a 5 mM concentration of bicarbonate.

Titration Experiments

Titration experiments were adapted from those previously carried out in the literature. Aliquots (usually between 5 and 20 µl) of the $Fe(NTA)_2$ solution were added to the transferrin and the spectrum recorded after each addition. This was repeated using aliquots of the $Re(NTA)_n$ solutions, but allowing 1.5 hours (or more when appropriate) between each addition to allow equilibration at 310 K.

Time Dependent Spectroscopy

Two molar equivalents of Re(NTA) solution were added to a transferrin or lactoferrin solution and the spectrum recorded at various time intervals. After equilibrium had been reached two molar equivalents of Fe(NTA)2 were added, and a further spectrum taken.

Reduction of $ReO_4^-$ 0.149 g of $Re_2O_7$ in 100 cm$^3$ water made a 0.006 M stock solution of $ReO_4^-$. 0.5 cm$^3$ of this solution were added to 1 cm$^3$ of $SnCl_2$ (0.006 M) along with 1 cm$^3$ of HCl (1 M). The reduction of the metal was then monitored by UV spectroscopy, in the presence of varying amounts of NTA. This process was also repeated using ascorbic acid as the reducing agent in place of $SnCl_2$.

These solutions were then used in the same manner as the rhenium atomic absorption standard, by raising the pH with microlitre amounts of 1 M NaOH and buffering in 10 mM Hepes. UV spectroscopy was used to monitor the effect of addition to transferrin.

Iron Binding to Transferrin

Figure 1:
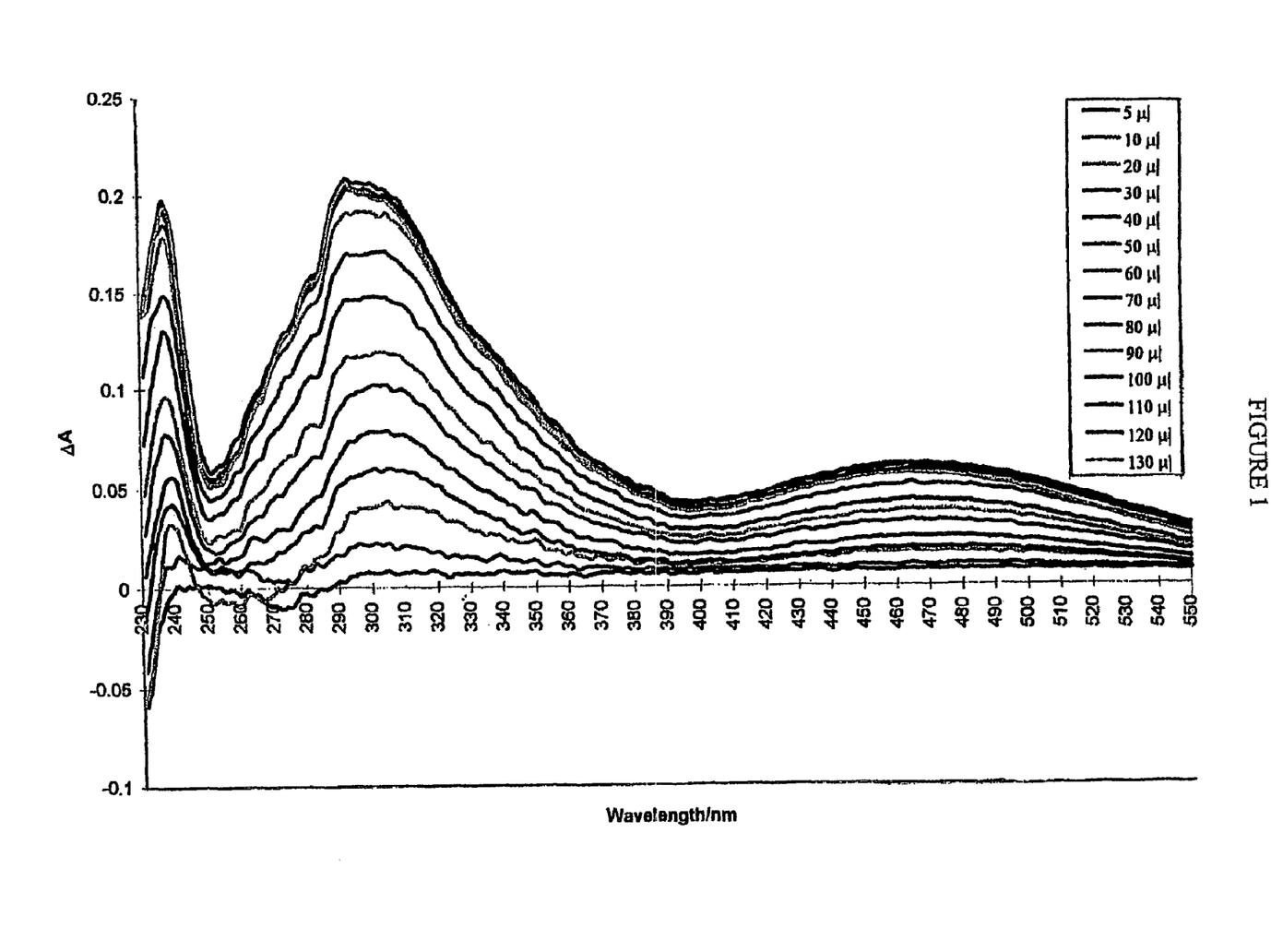
FIG. 1 illustrates the UV difference spectra for the titration of apotransferrin with Fe(NTA)$_2$.
Figure 2:
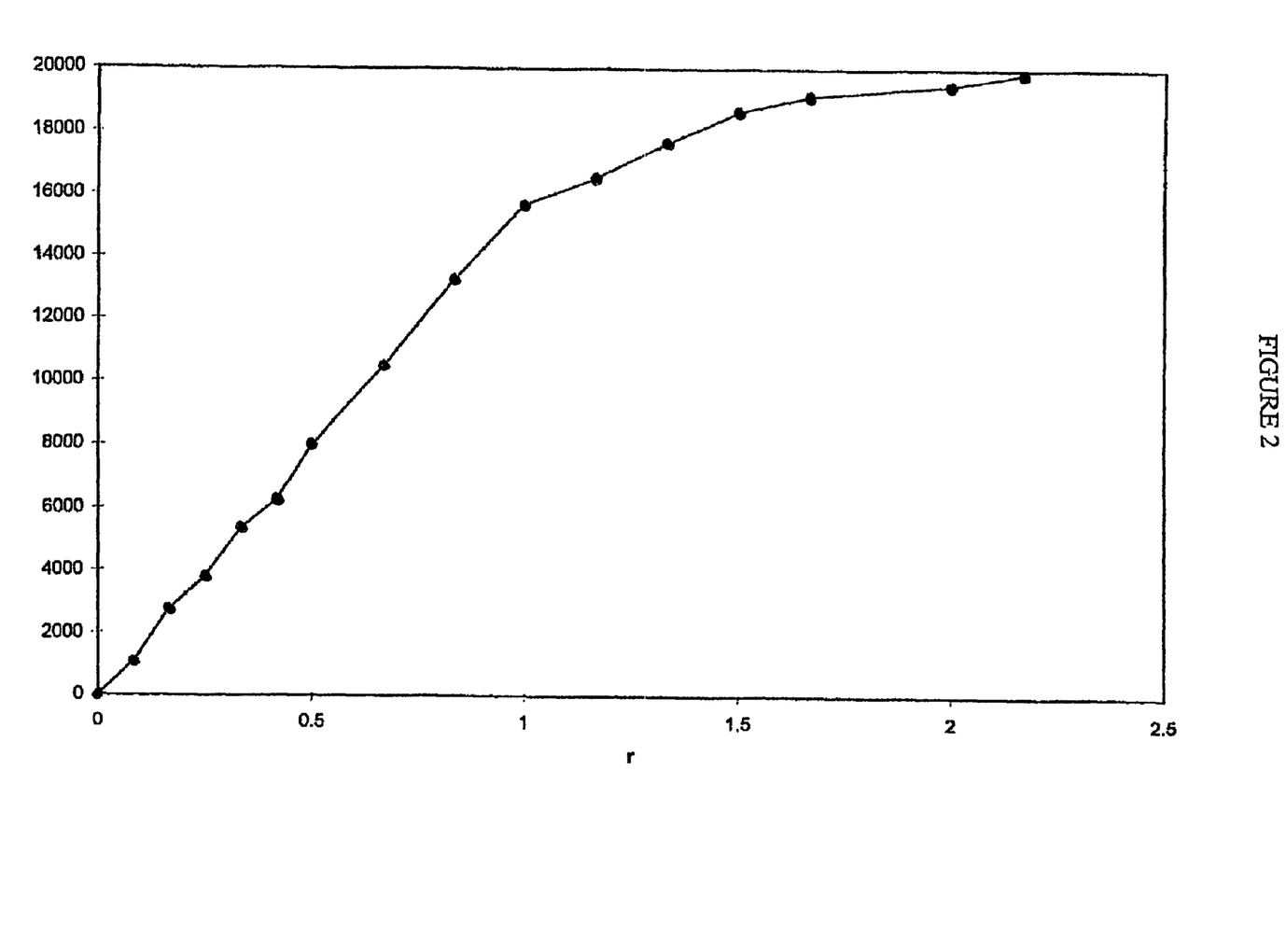
FIG. 2 illustrates a graph representing a titration curve for the addition of Fe(NTA)$_2$ to apotransferrin.

Upon iron binding the apotransferrin peak at 280 nm decreases in size, while two new peaks appear at 240 and 295 nm which provide a useful diagnostic test for metal binding. FIG. 1 shows the UV/vis difference spectra obtained after each addition of $Fe(NTA)_2$ during the titration experiment. The base line of all the UV difference spectra corresponds to apotransferrin before addition of any metal. The increase in absorbance at 240 and 295 nm is directly related to the percentage saturation of transferrin binding sites. The increase in absorbance at 240 nm was monitored and the change in molar extinction coefficient was determined. The ratio, r, of iron to transferrin was calculated (Table 1) and plotted against the change in extinction coefficient (FIG. 2). This shows a relationship between r and $\Delta\epsilon$ at low iron concentrations (when r is less than one). The slope of the linear portion of the graph was calculated to be 15800±210 M$^{-1}$ cm$^{-1}$ which equates to the molar absorptivity of transferrin with one site saturated with Fe. If we assume that the two sites are equivalent, we could expect the molar absorptivity for transferrin with both sites saturated with iron to be twice the magnitude at approximately 31600 M$^{-1}$ cm$^{-1}$. We believe these experiments demonstrate that iron binds strongly to the transferrin and that the transferrin protein remains intact during the substitution of iron into the transferrin.

TABLE I

Calculation of r and As values for Fe(NTA)2

| Volume Fe/μl | $10^{-6}$ [Tf]/ mol dm$^{-3}$ | r([Fe]/ [Tf]) | ΔA (240 nm) | Δε/M$^{-1}$ cm$^{-1}$ |
|---|---|---|---|---|
| 0 | 1.00 | 0.00 | 0.0000 | 0 |
| 5 | 9.98 | 0.08 | 0.0108 | 1083 |
| 10 | 9.97 | 0.17 | 0.0277 | 2778 |
| 15 | 9.95 | 0.25 | 0.0378 | 3803 |
| 20 | 9.93 | 0.33 | 0.0533 | 5369 |
| 25 | 9.92 | 0.42 | 0.0624 | 6293 |
| 30 | 9.9 | 0.50 | 0.0792 | 7997 |
| 40 | 9.87 | 0.67 | 0.1038 | 10514 |
| 50 | 9.84 | 0.83 | 0.1306 | 13272 |
| 60 | 9.8 | 1.00 | 0.1537 | 15686 |
| 70 | 9.77 | 1.17 | 0.1617 | 16551 |
| 80 | 9.74 | 1.33 | 0.1719 | 17654 |
| 90 | 9.71 | 1.50 | 0.1812 | 18659 |
| 100 | 9.68 | 1.67 | 0.1852 | 19128 |
| 120 | 9.62 | 2.00 | 0.1874 | 19478 |
| 130 | 9.58 | 2.17 | 0.1903 | 19865 |

Rhenium Binding to Transferrin

Addition of rhenium to transferrin also showed peaks due to tyrosine π-π* transitions, at 235 and 292 nm, although the second of these is significantly smaller in magnitude than for iron. No peak is seen in the visible region of the spectrum.

This is consistent with the spectra seen for some other metals such as gallium, neodymium, aluminium and indium with transferrin.

Figure 3:
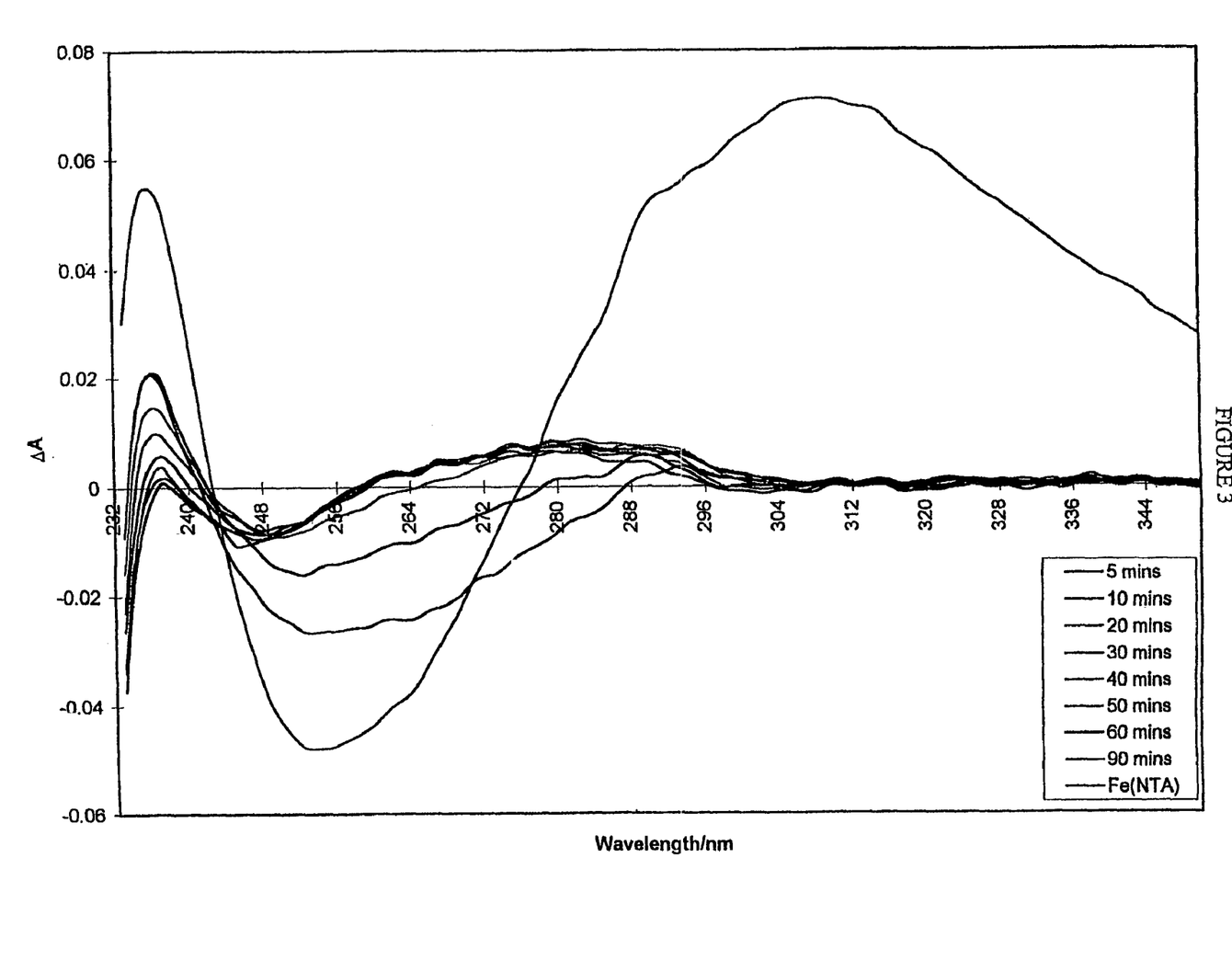
FIG. 3 illustrates the dependence of absorbance on time for a solution containing apotransferrin and 2 Molar equivalents Re(NTA).
Figure 4:
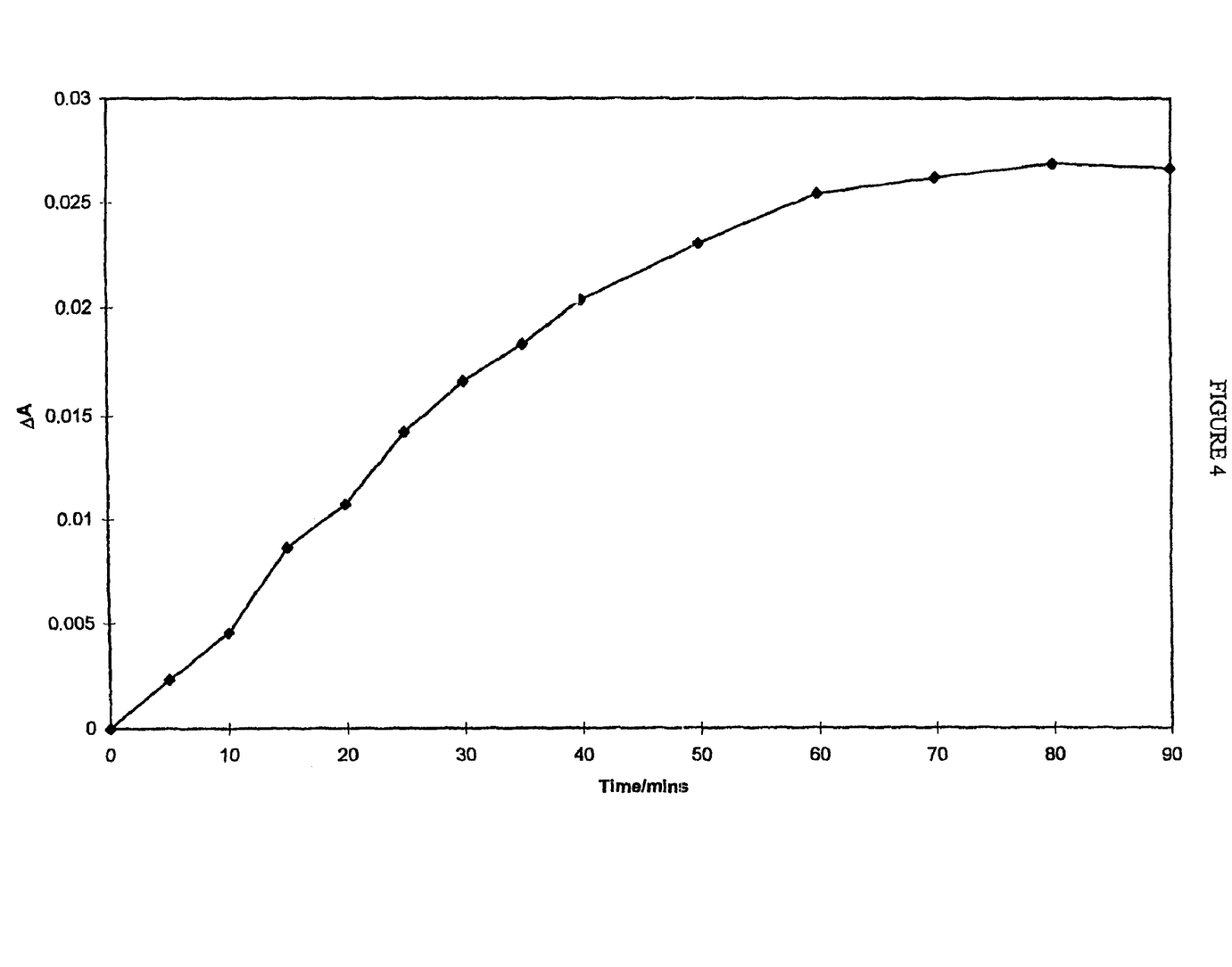
FIG. 4 illustrates a graph representing the dependence of A$_{235}$ on time for apotransferrin containing 2 Molar equivalents Re(NTA).

In contrast to the instantaneous binding shown by iron, the binding of rhenium to transferrin takes longer to reach an equilibrium. To assess this, two molar equivalents of Re(NTA) were added to the transferrin solution, and a spectrum taken at regular time intervals (FIG. 3). FIG. 4 shows the increase in absorbance at 235 nm with time and shows that at least an hour is required for the binding to reach completion.

Under other conditions, such as at temperatures lower than 310 K, or with more nitrilotriacetate present, the equilibration may take several hours. Once equilibrium was reached, two molar equivalents of Fe(NTA) were added to the solution and the spectrum obtained is shown by the blue line in FIG. 3. It can be seen that iron has a much faster rate of binding and much greater influence on the spectrum. However this slow binding does not appear to be unusual, and several metals are reported to require even longer for completion of binding. For example Sc(NTA)$_2$ needs at least 2 h to reach equilibrium and In(NTA)$_2$ requires approximately 6 hours'.

When Fe(NTA)$_2$ is added to rhenium transferrin (FIG. 3) the change in the spectrum is large and instantaneous. The transferrin has a much greater affinity for iron than for rhenium and so the rhenium is instantly displaced. This also occurs on the addition of iron to many other metal-transferrins including gallium and scandium.

Rhenium Titration Experiments

Figure 5:
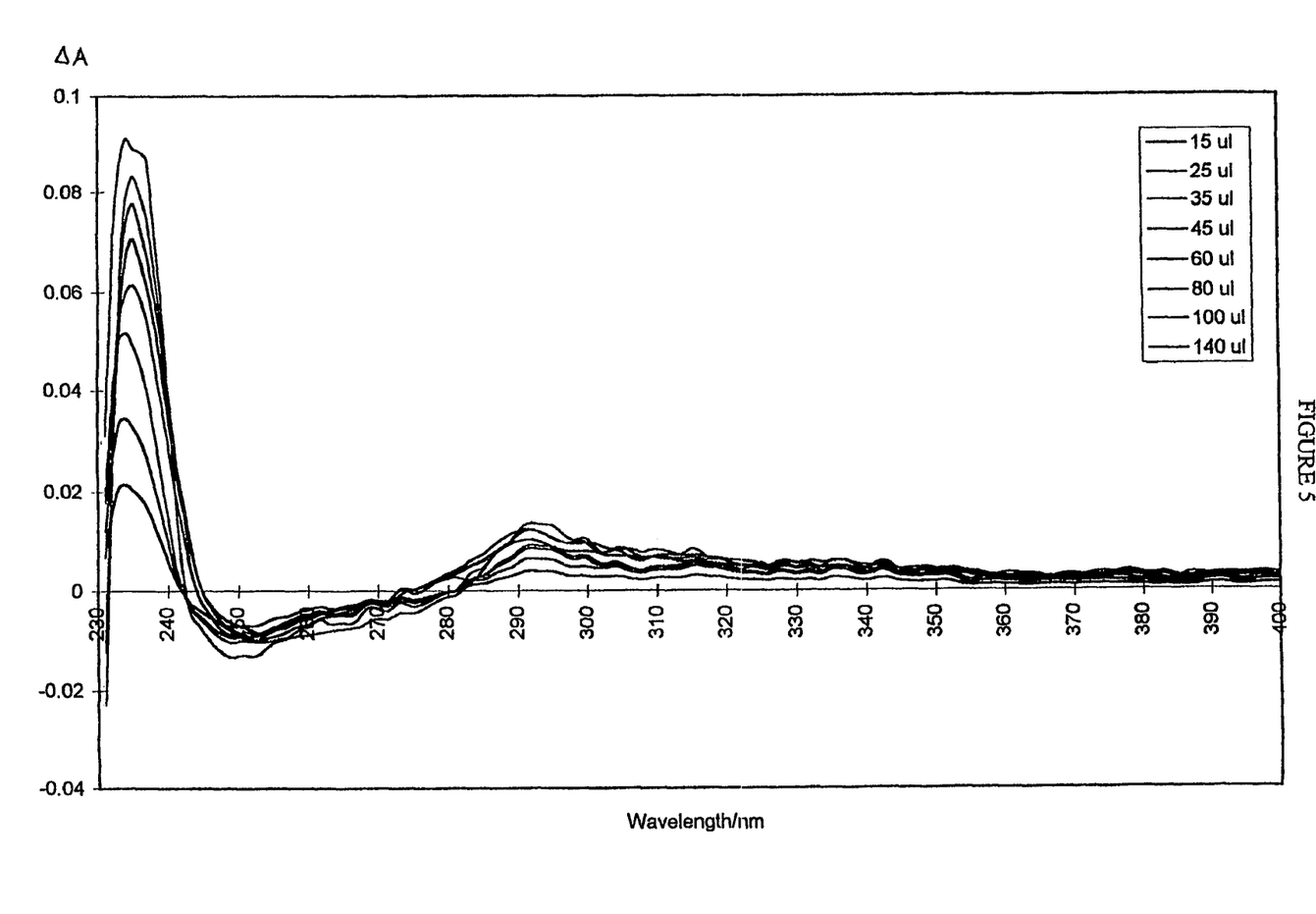
FIG. 5 illustrates the UV difference spectra for titration of apotransferrin with Re(NTA).

Apotransferrin was titrated with Re(NTA), Re(NTA)$_8$ and Re(NTA)$_{20}$, and the UV difference spectra recorded after allowing time for solutions to reach equilibrium (FIG. 5). The absorbance at 235 nm was converted to molar extinction coefficients, and the ratio, r, of rhenium to transferrin was calculated in the same way as for iron (Table 2).

TABLE 2

Calculation of r and Δε values for Re(NTA)$_n$

| Volume Re/μl | $10^{-6}$[Tf]/ mol dm$^{-3}$ | r ([Re]/ [Tf]) | ΔA(235 nm) | | | Δε/M$^{-1}$ cm$^{-1}$ | | |
|---|---|---|---|---|---|---|---|---|
| | | | Re(NTA) | Re(NTA)$_8$ | Re(NTA)$_{20}$ | Re(NTA) | Re(NTA)$_8$ | Re(NTA)$_{20}$ |
| 0 | 7.35 | 0.00 | 0.0000 | 0.0000 | 0.0000 | 0 | 0 | 0 |
| 5 | 7.34 | 0.11 | 0.0074 | 0.0073 | 0.0069 | 1012 | 1000 | 936 |
| 10 | 7.33 | 0.22 | 0.0138 | 0.0143 | 0.0140 | 1876 | 1950 | 1911 |
| 15 | 7.31 | 0.33 | 0.0213 | 0.0209 | 0.0211 | 2920 | 2856 | 2889 |
| 20 | 7.30 | 0.44 | 0.0279 | 0.0270 | 0.0251 | 3820 | 3700 | 3432 |
| 25 | 7.29 | 0.56 | 0.0350 | 0.0339 | 0.0292 | 4800 | 4650 | 4004 |
| 30 | 7.27 | 0.67 | 0.0423 | 0.0414 | 0.0336 | 5814 | 5700 | 4622 |
| 35 | 7.27 | 0.78 | 0.0491 | 0.0469 | 0.0362 | 6760 | 6450 | 4979 |
| 40 | 7.25 | 0.89 | 0.0551 | 0.0506 | 0.0383 | 7598 | 6980 | 5278 |
| 45 | 7.24 | 1.00 | 0.0625 | 0.0540 | 0.0392 | 8637 | 7456 | 5417 |
| 50 | 7.23 | 1.11 | 0.0666 | 0.0578 | 0.0403 | 9213 | 7999 | 5577 |
| 60 | 7.21 | 1.33 | 0.0729 | 0.0602 | 0.0417 | 10109 | 8349 | 5777 |
| 70 | 7.18 | 1.56 | 0.0767 | 0.0615 | 0.0430 | 10678 | 8563 | 5993 |
| 80 | 7.16 | 1.78 | 0.0795 | 0.0631 | 0.0437 | 11100 | 8807 | 6110 |
| 90 | 7.14 | 2.00 | 0.0816 | 0.0643 | 0.0454 | 11435 | 9000 | 6356 |
| 100 | 7.11 | 2.22 | 0.0832 | 0.0664 | 0.0453 | 11702 | 9340 | 6370 |
| 110 | 7.09 | 2.44 | 0.0842 | 0.0683 | 0.0454 | 11875 | 9629 | 6409 |
| 120 | 7.07 | 2.67 | 0.0849 | 0.0701 | 0.0464 | 12004 | 9922 | 6565 |
| 140 | 7.02 | 3.11 | 0.0887 | 0.0708 | 0.0467 | 12639 | 10085 | 6656 |

Rhenium Binding to Lactoferrin

Similar experiments were carried out with lactoferrin and rhenium. The data are described below. Re/NTA was then added to the apo-protein and the absorbance spectra recorded with time, to see if the Re was bound by the lactoferrin (FIGS. 6(A), (B) and (C) and FIG. 7). Both FIGS. 6(A), (B), (C) and 7 show that rhenium binds to lactoferrin, due to the increase in the 231 nm band upon rhenium binding.

Figure 6:
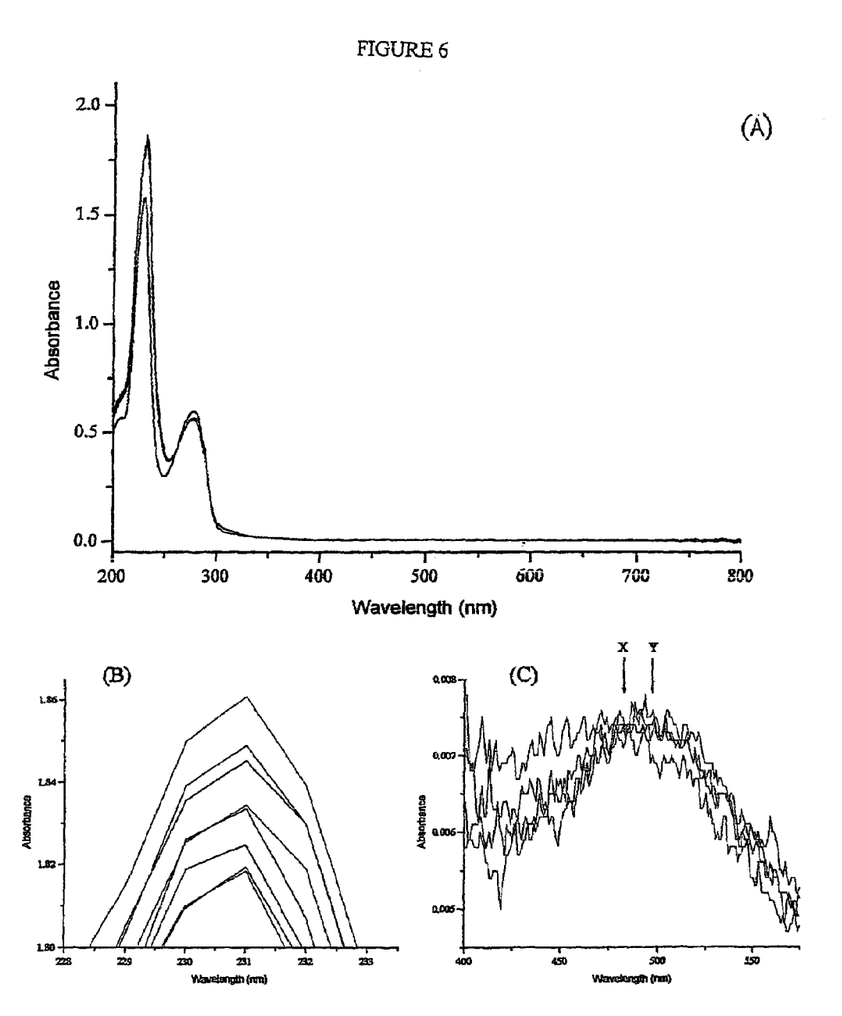
FIG. 6 illustrates a graph representing the reaction of apo-lactoferrin with Re/NTA, FIG. 6A showing 1×10$^{-5}$ M apo-lactoferrin and 5 mM sodium bicarbonate (black) then with 5-fold excess Re/NTA added after 0 mins, 15, 30, 90, 180, 240, 300, and 420 mm.

FIGS. 6(A), (B) and (C) represent the reaction of apo-lactoferrin with Re/NTA. 1×10$^{-5}$M apo-lactoferrin was added to 5 mM sodium bicarbonate (black) and then 5-fold excess Re/NTA was added after 0 mins, 15, 30, 90, 180, 240, 300 and 420 minutes. FIG. 6(B) shows the absorption peak at 231 nm, while FIG. 6(C) shows the absorption peak at 500 nm in more detail. X on FIG. 6(C) indicates the absorption peak at 0 and 15 minutes. Y on FIG. 6(C) indicates the shift in the maximum absorption wavelength at the end of the time course.

Figure 7:
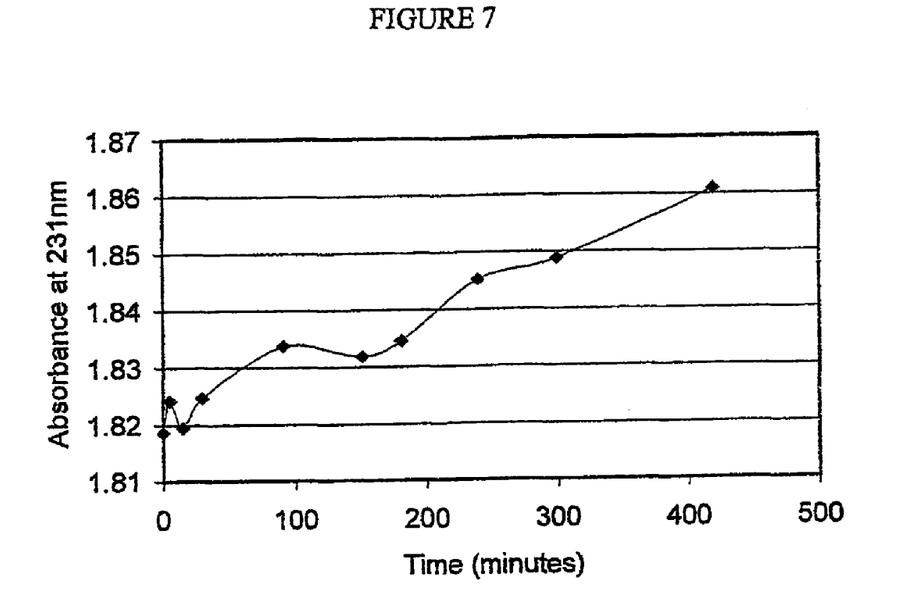
FIG. 7 illustrates a graph representing the reaction of apolactoferrin and sodium bicarbonate with excess Re/NTA, monitored by measuring absorbance at 231 nm with time.

FIG. 7 represents the reaction of apo-lactoferrin and sodium bicarbonate with excess Re/NTA. This reaction was monitored by measuring absorbance at 231 nm with time.

Both FIGS. 6(A), 6(B), 6(C) and 7 show that rhenium binds to lactoferrin, due to the increase in the 231 nm band upon rhenium binding.

We believe these experiments show that rhenium can be inserted into the binding site of transferrin, giving stable complexes within about 1 hour of addition. This chemistry is directly applicable to technetium chemistry with transferrin and lactoferrin, and by analogy—since the chemistry of technetium and rhenium are so similar—the same chemical protocol for rhenium binding to transferrin and lactoferrin may be used for technetium binding to the same proteins. The technetium experiments, because of the radioactive nature of technetium cannot be analysed in the same way. The experiments with technetium binding to transferrin and lactoferrin show directly the uptake of these species into tumour cells. These experiments are described below.

Example 2

Labelling of Transferrin with Technetium$^{99m}$ and Uptake of Tf-Tc Complex by Cancer Cells Experimental Procedure:

Stock Solutions

The following solutions were made up.
Pertechnetate Solution ($^{99m}$Tc) [TcO$_4^-$]:
270 MBq received in 1 ml aqueous solution. (Pertechnetate concentration: $5 \times 10^{-12}$ g/MBq ($3.06 \times 10^{-14}$ mol/MBq)) 50 MBq in 0.2 ml ($1.53 \times 10^{-12}$ M)

Apotransferrin solution (Tf):
Washed 3× with 0.1 M KCl. Final volume=1.2 ml Absorbance=0.65. (Extinction coefficient at 280 nm=93,000 M$^{-1}$ cm$^{-1}$). Total Tf=$8.4 \times 10^{-9}$ mol. Diluted in 5 ml. 0.025 ml diluted to 25 ml ($1.68 \times 10^{-12}$ mol/ml)

Tin (reducing) Solutions:
SnCl$_2$.2H$_2$O $34 \times 10^{-3}$ g+NaHCO$_3$ $4.4 \times 10^{-3}$ g+Fe(NO$_3$)$_3$ $12.5 \times 10^{-3}$ g in 25 ml: Working ion mixtures: 0.25 ml diluted to 25 ml and 0.025 ml of this diluted to 25 ml.

Solution Combinations

Following the Re chemistry described previously, the following combinations of solutions were mixed at room temperature for 1 h after which 10 ml of PBS was added and the solution mixed. 9 ml was then discarded and the remaining 1 ml diluted to 20 ml with PBS.

Solution: 1) 0.2 ml $^{99m}$Tc[TcO$_4^-$] solution+0.025 ml of tin solution.

2) 0.2 ml $^{99m}$Tc[TcO$_4^-$] solution+0.025 ml of tin solution+ 0.2 ml Tf.

Example 3

Uptake of Solutions by Cancer Cells

Each solution from Example 2 was incubated with cells as follows. Cell culture: RT112 cells seeded into four 25 cm flasks were grown to confluency in Dulbecco's Minimum Essential Medium +5% foetal bovine serum. 2 h prior to uptake studies the cells were washed once with Hanks balanced salt solution (HBSS) and incubated for 2 h at room temperature with 4 ml of HBSS. The cells were then washed with PBS and incubated for 1.5 h at room temperature with 4 ml of the corresponding (1–4) labelled incubation solution. The incubation solution was then discarded and the cells washed 5 × with PBS, treated with 2 ml of trypsin and 1 ml counted on a Packard gamma counter. A further flask was trypsinized to estimate cell number. Each solution was counted independently and the results averaged to give a measure of uptake.

Results

Figure 8:
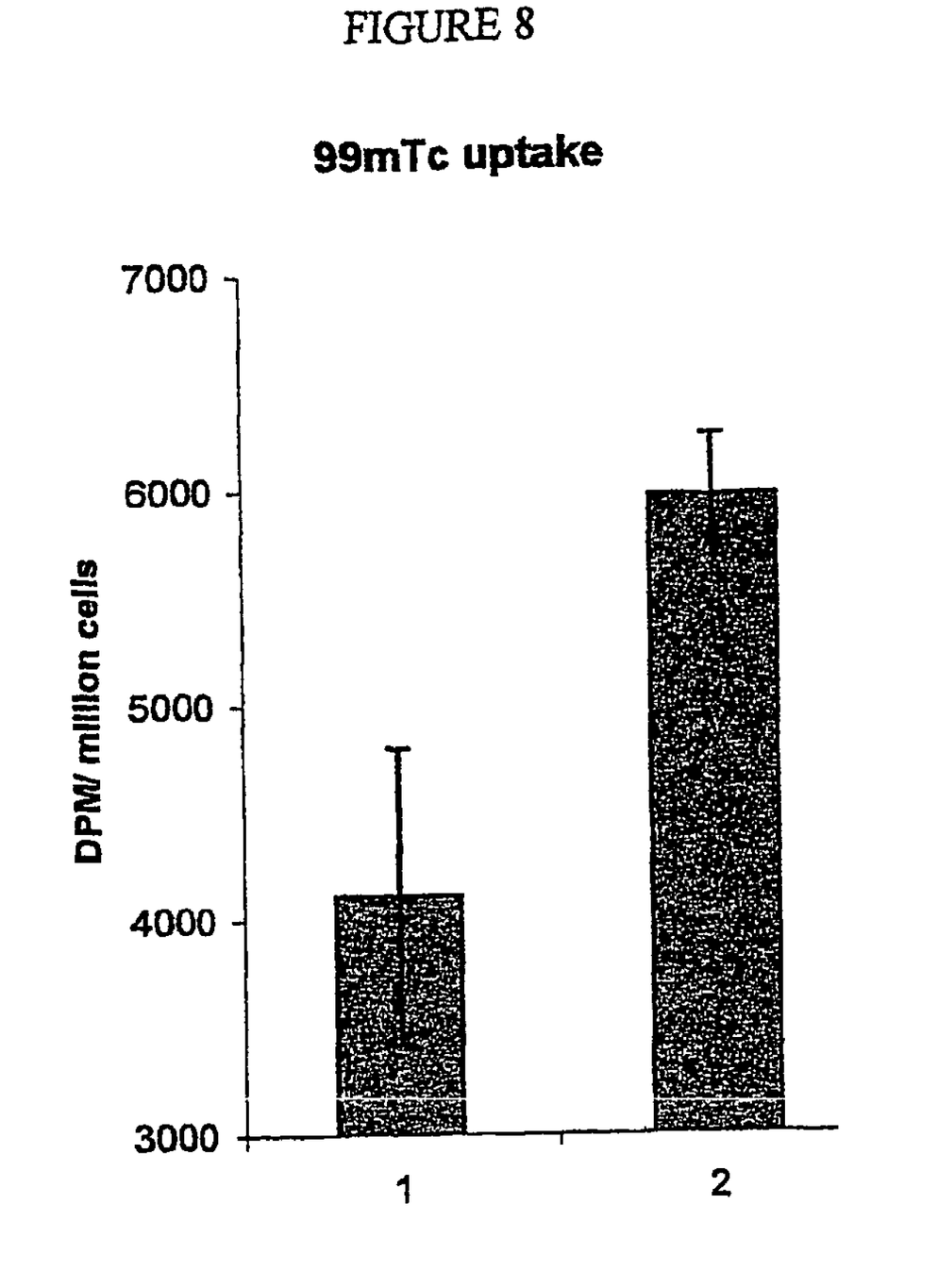
FIG. 8 illustrates a graph representing the uptake of the control Solution 1 (Tc$_4^-$ and reducing solution) and Solution 2 (TcO$_4^-$ and reducing solution and Tf).

In each case the Tc is taken-up by the tumour cells. Since the cells show phagocytotic behaviour, some non-specific uptake is expected. However, as FIG. 8 shows there is a clear enhancement of Tc uptake (by almost 50%) once it is complexed to the Tf.

Example 4

Preparation of Product

A product comprising the following components is made up as a lyophilised, pyrogen free powder:

| COMPOUND | AMOUNT mg |
| --- | --- |
| Lactoferrin | 40.0 |
| Tin(II)chloride | 0.24 |
| Gentisic acid | 0.84 |
| Sodium chloride | 30 |

The mixture is then placed in a vial and sealed. The mixture can then be stored at room temperature until required for use.

Example 5

Labelling Lactoferrin

The pertechnetate source is either sodium pertechnetate ($^{99m}$Tc) injection (Fission) or sodium pertechnetate ($^{99m}$Tc) (Non-Fission), maximum 7.4 GBq 200 mCi. An amount of the pertechnate is aseptically added to a volume of 3–6 ml aqueous solution in a vial and shaken and left for several minutes (2–5 minutes).

To prepare a dose for a single patient, the vial containing the lactoferrin and other additives is reconstituted in 3–6 ml saline solution and shaken for 2–5 minutes so as to allow the lyophilised material to reconstitute in solution. All but approximately 1 ml of the solution is withdrawn and added to the required amount of sodium pertechnetate ($^{99m}$Tc) injection (Fission) or sodium pertechnetate ($^{99m}$Tc) (Non-Fission). The mixture is then shaken to ensure a high labelling yield of lactoferrin.

Example 6

Detecting Tumour Site

A single dose of the $^{99m}$Tc labelled lactoferrin complex is administered by the i.v route and γ radiation is observed by conventional means over a selected period of time. The $^{99m}$Tc is found to concentrate in specific areas within the body, the area is found to correspond to a tumour site.

The invention claimed is:

1. A composition comprising lactoferrin and a reducing agent for converting Tc as the pertechnetate (TcO$_4^-$) to Tc$^{3+}$, wherein the lactoferrin is a serum lactoferrin.

2. A composition comprising lactoferrin and a reducing agent for converting To as the pertechnetate (TcO$_4^-$) to Tc$^{3+}$, which is in unit form and wherein the amount of lactoferrin per unit is in the range of 2–60 mg.

3. The composition according to claim 1 which is in unit form and wherein the amount of lactoferrin per unit is in the range of 2–60 mg.

4. A composition comprising lactoferrin and a reducing agent for converting Tc as the pertechnetate (TcO$_4^-$) to Tc$^{3+}$, which is in unit form and wherein the lactoferrin is derived from mammalian tissue or blood and the amount of lactoferrin per unit is in the range of 2–60 mg.

5. A composition comprising lactoferrin and a reducing agent for converting Tc as the pertechnetate (TcO$_4^-$) to Tc$^{3+}$, which is in unit form and wherein the lactoferrin is a recombinant protein and the amount of lactoferrin per unit is in the range of 2–60 mg.

6. The composition according to claim 1, further comprising a $^{99m}$Tc source.

7. A composition comprising lactoferrin and a reducing agent for converting Tc as the pertechnetate (TcO$_4^-$) to Tc$^{3+}$, wherein the lactoferrin is a recombinant protein, and further comprising a $^{99m}$Tc source.

8. The composition according to claim 6, wherein the $^{99m}$Tc source is pertechnetate TcO$_4$.

9. The composition according to claim 7, wherein the $^{99m}$Tc source is pertechnetate TcO$_4$.

10. A composition comprising lactoferrin and a reducing agent for converting Tc as the pertechnetate (TcO$_4^-$) to Tc$^{3-}$, further comprising a $^{99m}$Tc source, wherein the $^{99m}$Tc source is provided separately from the lactoferrin and reducing agent.

11. A composition comprising lactoferrin and a reducing agent for converting Tc as the pertechnetate (TcO$_4^-$) to Tc$^{3-}$, further comprising a $^{99m}$Tc source, wherein the amount of $^{99m}$Tc is about 7.4 GBq (200 mCi).

12. A composition comprising lactoferrin and a reducing agent for converting Tc as the pertechnetate (TcO$_4^-$) to Tc$^{3-}$, and further comprising a solubilizing agent and/or an isotonic agent.

13. The composition according to claim 12, wherein the solubilizing agent is gentisic acid.

14. The composition according to claim 12 which is in unit form and wherein the amount of solubilizing agent per unit is in the range of about 0.7 mg. to about 0.9 mg.

15. The composition according to claim 12, wherein the isotonic agent is sodium chloride.

16. The composition according to claim 12 which is in unit form and wherein the amount of isotonic agent per unit is in the range of about 20 mg to about 40 mg.

17. A composition comprising lactoferrin and a reducing agent for converting Tc as the pertechnetate (TcO$_4^-$) to Tc$^{3-}$, wherein the composition is lyophilized.

18. A composition comprising lactoferrin and a reducing agent for converting Tc as the pertechnetate (TcO$_4^-$) to Tc$^{3-}$, wherein the composition is in powder form.

19. A kit comprising a first composition comprising the lactoferrin and a reducing agent for converting Tc as the pertechnetate (TcO$_4^-$) to Tc$^{3-}$ in a first sealed vessel and a second composition comprising a radionuclide labeled lactoferrin complex in a second sealed vessel and optionally, a set of written instructions.

* * * * *